(12) United States Patent
Assmann

(10) Patent No.: US 9,162,592 B2
(45) Date of Patent: Oct. 20, 2015

(54) FITTING FOR VEHICLE SEAT

(75) Inventor: Uwe Assmann, Remscheid (DE)

(73) Assignee: KEIPER GMBH & CO. KG, Kaiserslautern (DE)

( * ) Notice: Subject to any disclaimer, the term of this patent is extended or adjusted under 35 U.S.C. 154(b) by 135 days.

(21) Appl. No.: 13/982,738

(22) PCT Filed: Feb. 17, 2012

(86) PCT No.: PCT/EP2012/000689
§ 371 (c)(1),
(2), (4) Date: Nov. 4, 2013

(87) PCT Pub. No.: WO2012/119698
PCT Pub. Date: Sep. 13, 2012

(65) Prior Publication Data
US 2015/0123444 A1    May 7, 2015

(30) Foreign Application Priority Data
Mar. 4, 2011 (DE) .......................... 10 2011 013 163

(51) Int. Cl.
*B60N 2/02* (2006.01)
*B60N 2/235* (2006.01)
(Continued)

(52) U.S. Cl.
CPC ................ *B60N 2/2356* (2013.01); *B60N 2/20* (2013.01); *B60N 2/2251* (2013.01); *B60N 2/682* (2013.01); *B60N 2/22* (2013.01); *B60N 2/235* (2013.01); *B60N 2205/20* (2013.01)

(58) Field of Classification Search
CPC ......... B60N 2/22; B60N 2/235; B60N 2/2356

USPC ........................ 297/366, 367 R, 367 P, 361.1
See application file for complete search history.

(56) References Cited

U.S. PATENT DOCUMENTS 5,769,494 A    6/1998 Barrere et al.
6,085,525 A *  7/2000 H.ang.kansson ............... 60/602
(Continued)

FOREIGN PATENT DOCUMENTS

CN    1926007 A    3/2007
DE    101 05 282 A1    8/2002
(Continued)

OTHER PUBLICATIONS

International Search Report in PCT/EP2012/000689 dated May 21, 2012.
(Continued)

*Primary Examiner* — Chi Q Nguyen
(74) *Attorney, Agent, or Firm* — Foley & Lardner LLP

(57) ABSTRACT

A fitting for a vehicle seat includes a first fitting part, a second fitting part which is rotatable relative to said first fitting part, a peripheral clamping ring which has a substantially L-shaped cross section, and which is connected to the first fitting part and extends over the second fitting part, and an intermediate ring which has a substantially L-shaped cross section, and which is arranged between the peripheral clamping ring and the second fitting part. A ledge is formed on the second fitting part, which ledge has an end surface and a cylindrical supporting surface. The supporting surface has a diameter which is smaller than the maximum outer diameter of the second fitting part, and the cylindrical supporting surface directly or indirectly supports the peripheral clamping ring.

14 Claims, 5 Drawing Sheets

(51) Int. Cl.
  *B60N 2/20*  (2006.01)
  *B60N 2/225*  (2006.01)
  *B60N 2/68*  (2006.01)
  *B60N 2/22*  (2006.01)

(56) References Cited

U.S. PATENT DOCUMENTS

| | | | |
|---|---|---|---|
| 6,112,370 A * | 9/2000 | Blanchard et al. | 16/325 |
| 6,629,733 B2 | 10/2003 | Matsuura et al. | |
| 6,758,525 B2 * | 7/2004 | Uramichi | 297/366 |
| 6,769,740 B2 * | 8/2004 | Yamada | 297/366 |
| 7,066,541 B2 | 6/2006 | Uramichi | |
| 7,100,987 B2 | 9/2006 | Volker et al. | |
| 7,261,379 B2 | 8/2007 | Volker et al. | |
| 7,293,837 B2 | 11/2007 | Assmann et al. | |
| 7,354,109 B2 | 4/2008 | Oki | |
| 7,677,667 B2 * | 3/2010 | Peters et al. | 297/367 R |
| 8,414,077 B2 * | 4/2013 | Reubeuze et al. | 297/367 P |
| 8,540,317 B2 * | 9/2013 | Stilleke et al. | 297/362.11 |
| 8,720,998 B2 * | 5/2014 | Stilleke | 297/367 R |
| 2002/0017811 A1 * | 2/2002 | Cilliere et al. | 297/367 |
| 2006/0012232 A1 * | 1/2006 | Coughlin et al. | 297/367 |
| 2007/0289092 A1 | 12/2007 | Rohee et al. | |
| 2012/0169105 A1 * | 7/2012 | Assmann et al. | 297/367 P |

FOREIGN PATENT DOCUMENTS

| | | |
|---|---|---|
| DE | 101 20 854 C1 | 8/2002 |
| DE | 10 2005 0 46 807 B3 | 11/2006 |
| DE | 10 2006 0 15 560 B3 | 8/2007 |
| DE | 10 2004 0 10 491 B4 | 4/2008 |
| DE | 10 2008 0 24 052 A1 | 11/2009 |
| EP | 1 676 502 A2 | 7/2006 |
| FR | 2578602 A1 | 9/1986 |
| FR | 2900605 A1 | 11/2007 |
| JP | 2007-526052 A | 9/2007 |
| KR | 10-2008-0107347 A | 12/2008 |

OTHER PUBLICATIONS

Office Action issued in co-pending Chinese Application No. 201280004635.8 dated Feb. 4, 2015.

Office Action issued in co-pending Korean Application No. 10-2013-1026311 dated Jan. 29, 2015.

* cited by examiner

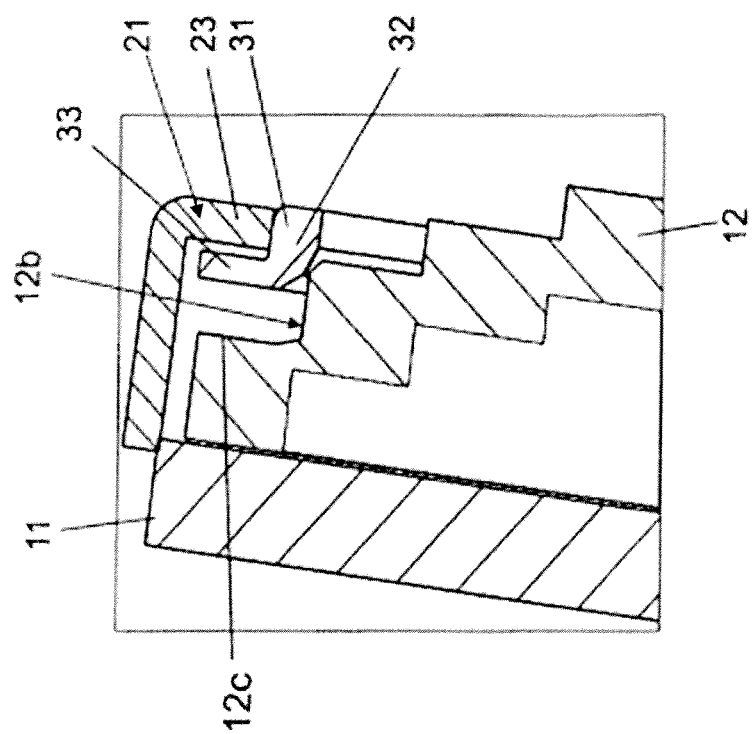
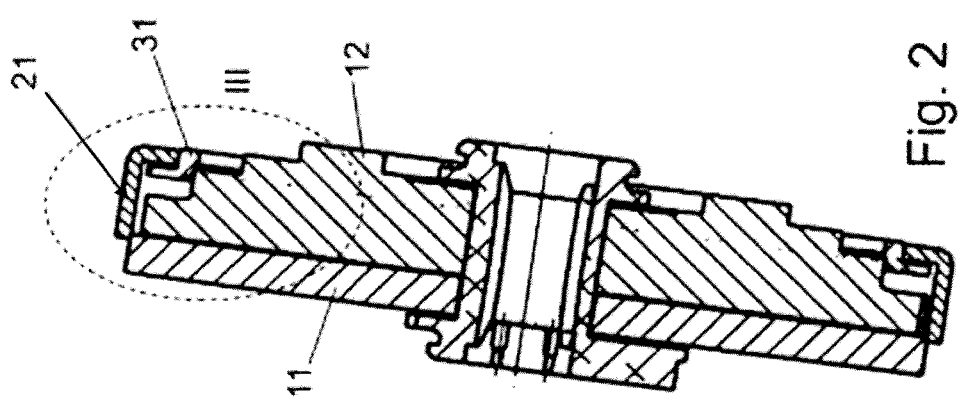

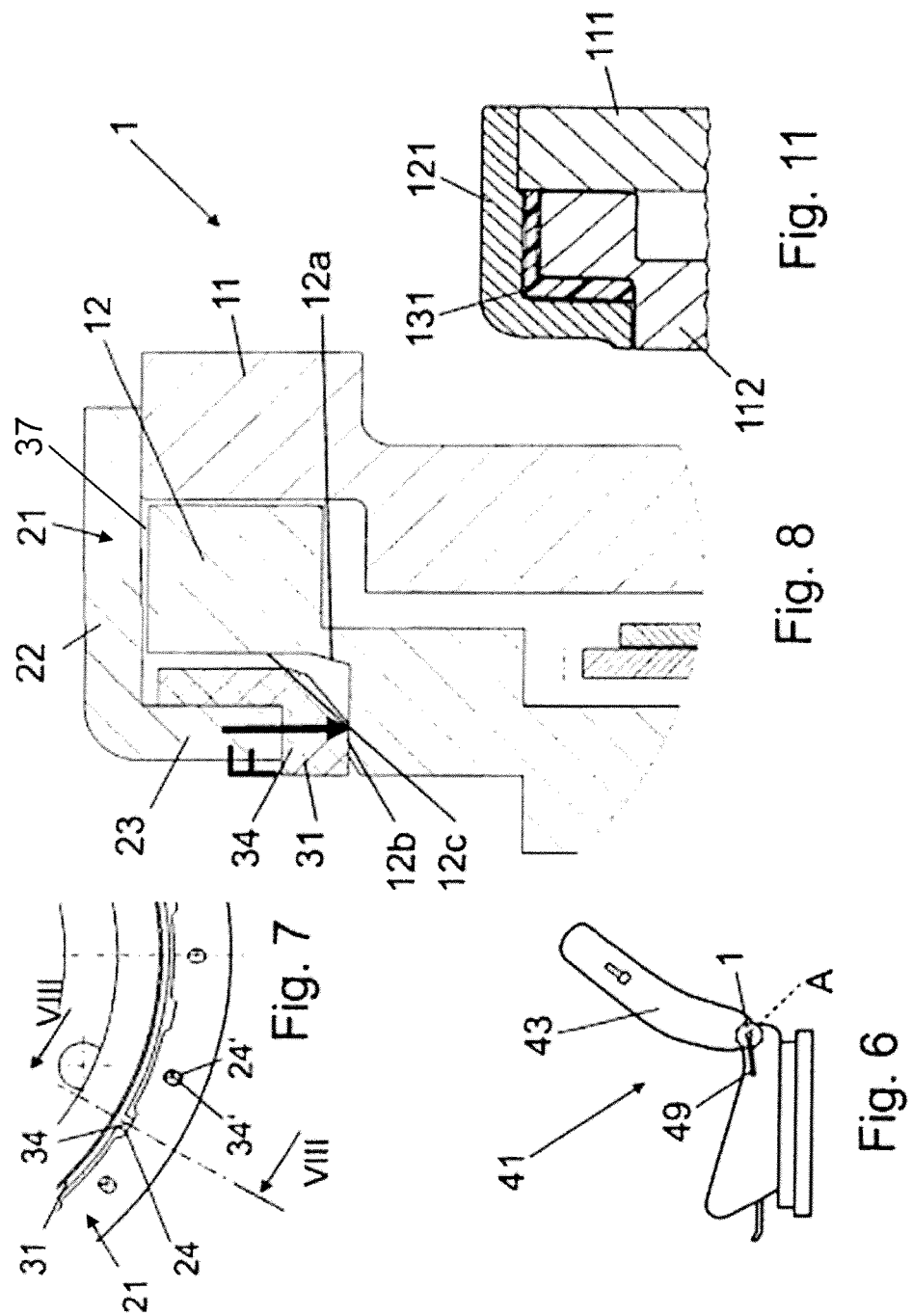

FITTING FOR VEHICLE SEAT

CROSS REFERENCE TO RELATED APPLICATIONS

The present application is a National Stage of International Application No. PCT/EP2012/000689 filed on Feb. 17, 2012, which claims the benefit of German Patent Application No. 10 2011 013 163.9 filed on Mar. 4, 2011, the entire disclosures of which are incorporated herein by reference.

FIELD

The invention relates to a fitting for a vehicle seat, in particular for a motor vehicle seat, having the features of the preamble of claim 1.

BACKGROUND

EP1676502 A2 discloses a fitting which provides for a direct bearing of the metal fitting members on each other in the region of the outer periphery of the second fitting member, the clamping ring being of L-like form, being securely connected to the first fitting member at the outer periphery thereof or in the immediate vicinity thereof, having a cylindrical region and an inwardly extending edge region, wherein it engages behind the outer peripheral region of the second fitting member with the inwardly extending edge region and is in sliding contact with an outwardly directed lateral face of the first fitting member by means of a plurality of protrusions which project in an axial direction in the direction of the first fitting member. The bearing in a radial direction may be brought about either by means of the clamping ring or—alternatively—by means of the first fitting member which has a corresponding shoulder in the region of the outer periphery. This results in an unfavorable friction coefficient of the metal/metal material pairing.

DE102004010491 B4 discloses a fitting for a vehicle seat, of which a section is illustrated in the drawings. This fitting has a first fitting member 111, a second fitting member 112 which is supported on the first fitting member 111 and which is rotatable relative thereto about a center axis, and a clamping ring 121 which is connected to the first fitting member 111 and engages over the second fitting member in order to axially secure it. In this instance, a plastics intermediate ring 131, which is of L-like form and which is positioned in accordance with the L-like clamping ring 121 so as to extend on the inner surface and inner lateral face thereof, is arranged between the L-like clamping ring 121 and the second fitting member 112. The intermediate ring 131 is connected to the second fitting member 112 in a rotationally secure manner and supports the first fitting member 111 in a radial direction with a bearing face which is formed by the inner surface of the cylindrical region and, in an axial direction, by the end face which extends in a radial direction.

SUMMARY

An object of the invention is to improve a fitting of the type mentioned in the introduction. This object is achieved according to the invention by a fitting having the features of claim 1. The dependent claims relate to advantageous embodiments.

In this instance, a shoulder which is offset inwards relative to the maximum outer diameter and which has an end face which extends outwards in a radial direction and a cylindrical bearing face is constructed on the second fitting member, with the bearing face having a diameter which is smaller than the maximum outer diameter of the second fitting member, and the cylindrical bearing face supporting the clamping ring directly or indirectly, in particular preferably by means of an intermediate ring which is connected to the clamping ring in a rotationally secure manner. In contrast to the prior art, in this instance the bearing face is displaced from a position on the outer periphery of the second fitting member radially inwards, in the direction of the center axis of the fitting. In this instance, at least a region having a maximum outer diameter of the second fitting member projects radially outwards beyond the bearing face constructed on the second fitting member, that region being able to form a support for the clamping ring in the event of a crash, and thereby increasing the crash safety. In normal operation, however, that region is not in contact with the clamping ring.

In a particularly preferable manner, there is provided an intermediate ring which is connected in a rotationally secure manner to the clamping ring and which is supported at its inner surface on a shoulder of the second fitting member. By an intermediate ring being arranged between the clamping ring and a shoulder of the second fitting member, the play necessary for actuation can be compensated for in such a manner that disruptive rattling noises are also not produced without a backrest compensation spring. In order to keep the wear low, that is to say, to limit it to a small number of selected locations, the intermediate ring is carried in a rotationally secure manner by the clamping ring.

The clamping ring preferably has means for retaining the intermediate ring in a rotationally secure manner. Those means can be formed in particular by receiving members on the clamping ring and cams on the intermediate ring and/or by openings in the clamping ring and studs on the intermediate ring. However, it is also possible to have any other means for retaining the intermediate ring on the clamping ring in a rotationally secure manner.

The intermediate ring preferably has, for retaining the intermediate ring on the clamping ring in a rotationally secure manner, at least three cams, in particular preferably precisely six cams, which extend outwards in a radial direction from a substantially hollow-cylindrical region. Those cams become deformed resiliently and/or plastically when the fitting is assembled. The clamping ring preferably has at least a number of recesses which corresponds to the number of cams, by which recesses the cams are received. In this instance, the number may be twice, three times or four times as large, whereby the number of possible orientations of the intermediate ring in the clamping ring is increased.

The intermediate ring preferably has, for retaining the intermediate ring on the clamping ring in a rotationally secure manner, at least three studs, in particular preferably precisely six studs, which extend in an axial direction in the direction of the clamping ring from the edge region of the intermediate ring extending in a radial direction. The clamping ring has at least a corresponding number of openings in which the studs are positioned during assembly.

In a particularly preferable manner, the second fitting member and the intermediate ring are provided with chamfers in order to make it easier to push the intermediate ring onto the shoulder of the second fitting member. Damage to the sliding face of the intermediate ring is also thereby prevented.

The intermediate ring applies a radial pretensioning force to the second fitting member when the fitting is in the assembled state so that the second fitting member is retained in a centered state relative to the clamping ring (and therefore in relation to the first fitting member).

During correct use, a radial gap is provided between the second fitting member and the clamping ring whereas, in the event of a crash, there may be brought about additional direct support of the second fitting member on the clamping ring.

The fitting according to the invention can be used in a versatile manner, for example, in order to couple the backrest of a vehicle seat, to adjust the inclination of a thigh support or to otherwise fold and lock a member of the vehicle seat. The fitting may be a locking fitting as described, for example, in DE10105282 A1, or be constructed as a gear fitting, as described, for example, in DE10120854 C1, with two internal-toothed wheels and a central planet wheel.

BRIEF DESCRIPTION OF THE DRAWINGS

The invention is explained in greater detail below with reference to two embodiments illustrated in the drawings, in which:

FIG. 2 is a cross section transversely through a fitting during the assembly, FIG. 3 is a detailed view of the detail III of FIG. 2, FIG. 6 is a schematic illustration of a vehicle seat having fittings according to the invention, FIG. 7 is a detailed view of the outer region of the fitting, FIG. 8 is a section along line VIII-VIII in FIG. 7, FIG. 10 is a section through the bearing region according to the second embodiment and FIG. 11 is a section through a fitting according to the prior art.

DETAILED DESCRIPTION

Figure 1:
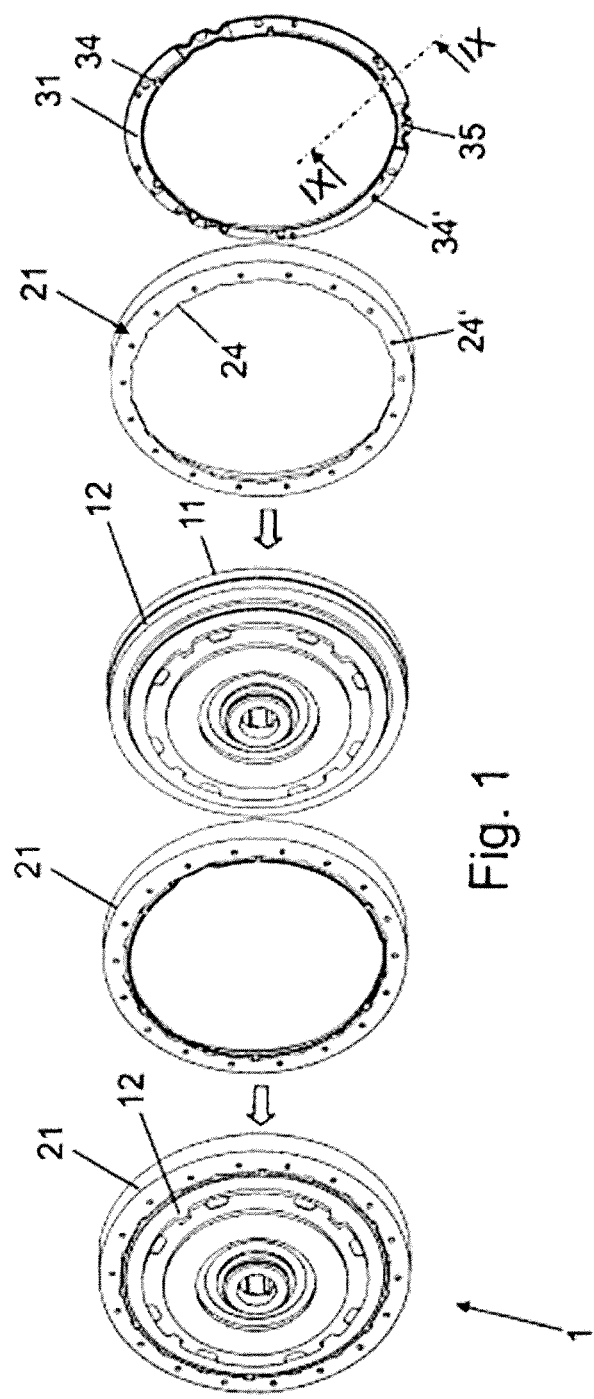
FIG. 1 is a three-part illustration of the first embodiment which shows three assembly steps—which are illustrated from right to left—for assembling a fitting according to the embodiment, only a clamping ring and an intermediate ring being illustrated in the first step.

In the first embodiment, a fitting 1 in the form of a locking fitting has an approximately plate-like first fitting member 11 and a second fitting member 12 which is also approximately plate-like, which are rotatable relative to each other about a center axis A. The following direction indications relate to the cylindrical coordinate system which is defined by that center axis A.

As described in DE10105282 A1, whose disclosure content is expressly incorporated herein by reference, there are constructed on the first fitting member 11 guide segments which together guide at least one, in this instance two, radially movable, toothed bar(s) which cooperate(s) with a toothed ring of the second fitting member 12 in the form of an internal-toothed wheel in order to lock the fitting 1.

A clamping ring 21 which is substantially L-shaped in cross section has, on the one hand, a substantially hollow-cylindrical region 22 which extends in a peripheral direction and with which it is arranged on the radially outwardly directed peripheral face of the first fitting member 11 and is securely connected thereto. On the other hand, the clamping ring 21 has, on the end face thereof facing away from the first fitting member 11, an edge 23 which extends over the second fitting member 12 so as to form an annular end face and secures it in an axial direction. In a radial direction, play is provided between the second fitting member 12 and the clamping ring 21 in order to allow unimpeded rotational movement of the second fitting member 12.

Figure 5:
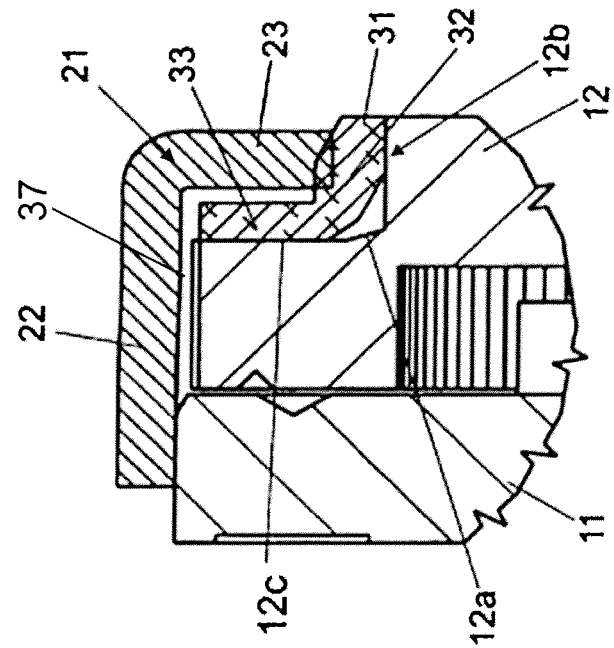
FIG. 5 is a cross section through the outer region of the fitting after complete assembly.
Figure 4:
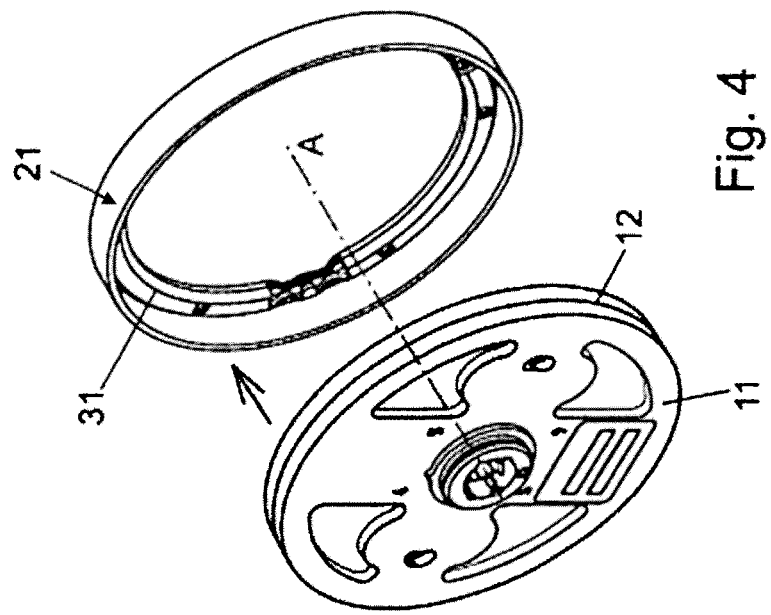
FIG. 4 is another perspective illustration of the second assembly step of FIG. 1.

A plastics intermediate ring 31 which is substantially L-like in cross section and which is arranged on a shoulder 12a, which is located radially not completely at the outer side (formed by a cylindrical bearing face 12b and an end face 12c which extends outwards substantially in a radial direction) on a bearing face 12b of the second fitting member 12, is arranged in the region between the second fitting member 12 and the clamping ring 21, which ring 31 has, in a transposed arrangement relative to the clamping ring 21, an inner, substantially hollow-cylindrical region 32 and an adjoining, outwardly extending, annular edge region 33. Consequently, the edge region 33 of the intermediate ring 31 extending transversely relative to the axial direction is positioned between the edge 23 of the clamping ring 21 and the second fitting member 12. The hollow-cylindrical region 32 of the intermediate ring 31 is positioned on the substantially cylindrical inner peripheral face of the annular edge 23 of the clamping ring 21 and rotatably positioned on a substantially cylindrical outer surface of the shoulder 12a of the second fitting member 12 which forms the said bearing face 12b so that this region forms the bearing between the arrangement comprising the first fitting member 11 and the clamping ring 21 and intermediate ring 31 and the second fitting member 12, that is to say, it supports the first fitting member 11 on the second fitting member 12. In principle, the intermediate ring 31 may also be dispensed with (cf. second embodiment) so that the first fitting member 11 is supported directly on the second fitting member 12 by means of the clamping ring 21 which is securely connected thereto. According to the illustration of FIG. 5, the intermediate ring 31 adjoins, by means of its lateral face directed towards the second fitting member 12, that face of the shoulder 12a extending in a radial direction, but a spacing may also be provided in this region, as illustrated in FIG. 8. In this instance, it may be seen in FIG. 5 that the resilient/plastic deformation of the intermediate ring 31 which is produced during the assembly of the fitting 1 is not illustrated but instead an intersection of the intermediate ring 31 and the clamping ring 21 in the region of the cams 34 is illustrated. However, FIG. 8 shows the deformed intermediate ring 31.

The intermediate ring 31 has at least three, in this instance six, cams 34 which extend in a radial direction outwards into correspondingly deep receiving members 24 in the clamping ring 21, which receiving members are, however, constructed to be larger in a peripheral direction (see FIG. 7). Furthermore, the intermediate ring 31 has studs 34' which extend in an axial direction from the edge region 33 of the intermediate ring 31 in the direction of the clamping ring 24 and which are received in corresponding openings 24' of the clamping ring 21. That arrangement ensures a rotationally secure carrying movement of the intermediate ring 31 by the clamping ring 21. However, the rotationally secure carrying movement may also be brought about in any other suitable manner and, in particular, for example, only the cams 34 may be provided in conjunction with the receiving members 24 or only the studs 34' may be provided in conjunction with the openings 24' of the clamping ring 21.

Furthermore, three resilient regions 35 are constructed on the intermediate ring 31 and extend outwards in a radial direction from the hollow-cylindrical region 32 and adjoin the inner side of the clamping ring 21. Any tolerances, for example, diameter tolerances owing to water absorbed by the intermediate ring 31, are thereby compensated for without the relative rotation between the first and second fitting members being impeded. The cams 34 further have a damping action.

The intermediate ring 31 is constructed so as to have a plurality of chamfers, a first chamfer provided on the outer periphery assisting during insertion of the intermediate ring 31 into the clamping ring 21, that is to say, acting as an inclined introduction member. A stepped chamfer is constructed at the inner periphery at the side of the edge region 33, the edge-side region being a space for adaptation to the form of the shoulder 12a in this region, and the region adjacent to the inner surface acts as an inclined introduction member for fitting to the second fitting member 12 and prevents damage to the inner surface which is rotatably supported on the bearing face 12b of the second fitting member 12 during use.

The fitting 1 is assembled as follows: in a first step, the fitting members 11 and 12—independently of each other—and the additional elements which are not described in greater detail and which are arranged between the two fitting members 11 and 12 are preassembled and, in a separate manner, the intermediate ring 31 is inserted into the clamping ring 21, as illustrated on the right in FIG. 1. Subsequently, the subassembly comprising the intermediate ring and clamping ring is placed on the fitting member subassembly and the two subassemblies are pressed together.

In this instance, the intermediate ring 31 has a slight overdimension in the region of the cams 34 before assembly. In order to simplify the pressing-together, the shoulder 12a and the corresponding region of the intermediate ring 31 have a chamfer (or rounding), as can be seen in FIG. 8. This can also be seen accordingly in the illustration of FIG. 3 which shows a slightly modified intermediate ring 31. Another bevelling or chamfering is provided on the outer edge of the intermediate ring 31 and the corresponding inner edge of the shoulder 12a.

By being pressed together, the height of the cams 34 is reduced, the intermediate ring 31 becoming adapted to the geometry of the clamping ring 21 during assembly with resilient and/or plastic deformation. Owing to the cams 34 in conjunction with the receiving members 24 and the studs 34' in conjunction with the openings 24', the intermediate ring 31 is positioned in the clamping ring 21 in a rotationally secure manner. Furthermore, a given pretensioning force F, as indicated in FIG. 8, acts between the intermediate ring 31 and the second fitting member 12, that is to say, the second fitting member 12 is supported with radial pretensioning.

Figure 10:
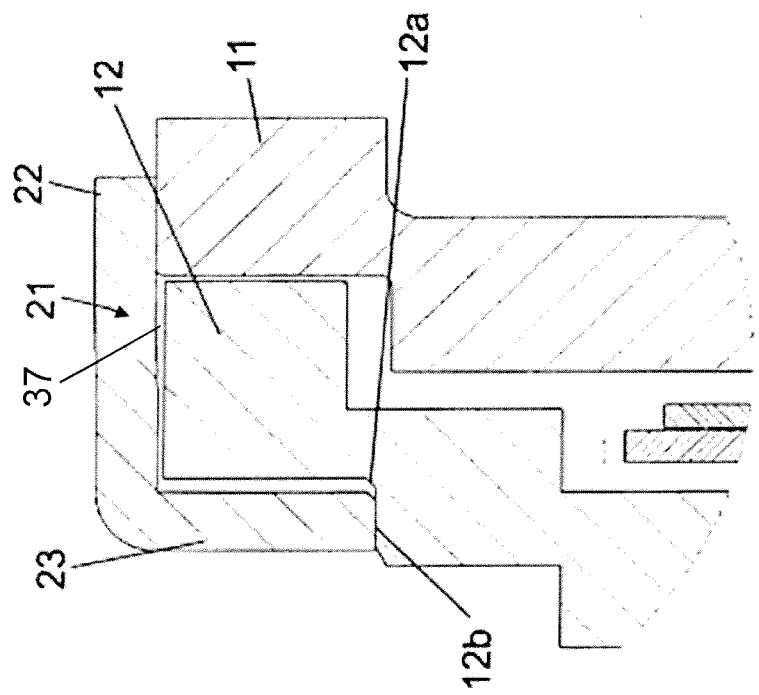
Figure 9:
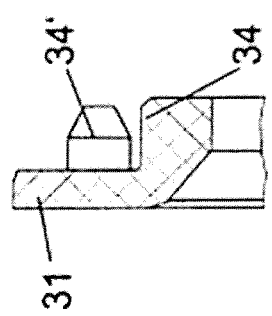
FIG. 9 is a section along line IX-IX in FIG. 1.

According to the second embodiment schematically illustrated in FIG. 10, the intermediate ring is dispensed with. In this instance, the intermediate ring 21 is securely connected to the first fitting member 11 in accordance with the first embodiment in the hollow-cylindrical region 22 thereof. Unlike the first embodiment, the edge 23 is drawn inwards further in a radial direction so that the inner surface of the edge 23 is directly in abutment with the bearing face 12b of the shoulder 12a of the second fitting member 12. Otherwise, the second embodiment corresponds to the first embodiment so that it is not discussed in greater detail.

According to a variant of the second embodiment which is not illustrated in the drawings, the end region of the clamping ring 21 in which the second fitting member is supported is provided with a friction-reducing coating.

In order to increase the safety, in particular the crash safety, the outer periphery of the second fitting member 12 has such dimensions that the outer surface can further be directly supported on the clamping ring 21 in the event of great loads, particularly without the intermediate ring 31 being arranged therebetween. During normal operation, however, a gap 37 is located between the two members, that gap 37 being able to be filled with lubricant in order to provide a damping layer and to prevent noise in the (undesirable) event of radial contact.

The fitting 1 according to the invention may be used in a vehicle seat 41 for a motor vehicle, for example, for adjusting the inclination, folding in a table-like manner or coupling of the backrest 43 thereof in some other manner. In general, a manually actuatable hand-operated lever 49 is located on a transmission rod which is aligned with the center axis A between two fittings 1 according to the invention and ensures synchronous unlocking thereof.

LIST OF REFERENCE NUMERALS

1 Fitting
11 First fitting member
12 Second fitting member
12a Shoulder
12b Bearing face
12c End face
21 Clamping ring
22 Hollow-cylindrical region
23 Edge
24 Recess
24' Opening
31 Intermediate ring
32 Hollow-cylindrical region
33 Edge region
34 Cams
34' Studs
35 Resilient region,
37 Gap
41 Vehicle seat
43 Backrest
49 Hand-operated lever
A Center axis
F Radial pretensioning force

PRIOR ART

111 First fitting member
112 Second fitting member
121 Clamping ring
131 Intermediate ring

What is claimed is:
1. A fitting for a vehicle seat, comprising:
a first fitting member;
a second fitting member which is rotatable relative thereto about a center axis; and
a clamping ring which is substantially L-shaped in cross section, wherein the clamping ring has a hollow-cylindrical region and an edge, wherein the hollow-cylindrical region is located on a radially outwardly directed peripheral face of the first fitting member and is securely connected to that first fitting member, wherein the edge is located at an end face of the clamping ring facing away from the first fitting member, wherein the edge is drawn inwards in a radial direction and engages over the second fitting member so as to form an annular end face and rotatably secures the clamping ring to the second fitting member relative to the first fitting member,
wherein the second fitting member has a shoulder which is offset radially inwards relative to a maximum outer diameter and which has an end face which extends outwards in a radial direction and a cylindrical bearing face, with the cylindrical bearing face having a diameter which is smaller than the maximum outer diameter of the second fitting member, and the cylindrical bearing face supporting the edge of the clamping ring directly or indirectly.

2. The fitting as claimed in claim 1, comprising an intermediate ring which is arranged between the clamping ring and the second fitting member, with the intermediate ring being arranged between the edge of the clamping ring and the shoulder of the second fitting member.

3. The fitting as claimed in claim 2, wherein the intermediate ring has a hollow-cylindrical region and an edge region, with the second fitting member being supported on the hollow-cylindrical region of the intermediate ring on the inner surface thereof.

4. The fitting as claimed in claim 3, wherein there is constructed on the intermediate ring at least one resilient region which extends out of the hollow-cylindrical region outwards in a radial direction and adjoins the inner side of the clamping ring.

5. The fitting as claimed in claim 4, wherein precisely three resilient regions are constructed on the intermediate ring.

6. The fitting as claimed in claim 2, wherein the clamping ring has structure that secures the intermediate ring in a rotationally secure manner.

7. The fitting as claimed in claim 6, wherein the intermediate ring has at least one of cams and studs which cooperate with corresponding recesses or openings of the clamping ring.

8. The fitting as claimed in claim 2, wherein the second fitting member and the intermediate ring are provided with chamfers in order to allow the intermediate ring to be easily pushed onto the shoulder of the second fitting member.

9. The fitting as claimed in claim 2, wherein the intermediate ring applies a radial pretensioning force to the second fitting member.

10. The fitting as claimed in claim 1, wherein, during correct use of the fitting, a gap is provided between the outer periphery of the second fitting member and the clamping ring, and in that, in the event of a crash, additional direct support of the second fitting member on the clamping ring is possible.

11. The fitting as claimed in claim 10, wherein a lubricant is received in the gap.

12. The fitting as claimed in claim 1, wherein the inner surface of the edge is in direct abutment with the bearing face of the shoulder of the second fitting member.

13. The fitting as claimed in claim 12, wherein the end region of the clamping ring in which the second fitting member is supported is provided with a friction-reducing coating.

14. A vehicle seat having a backrest and comprising a fitting as claimed in claim 1 for coupling the backrest.

\* \* \* \* \*